United States Patent [19]

Zimmerman

[11] 4,141,893
[45] Feb. 27, 1979

[54] DECAHYDROCYCLOPENT[c]AZEPINES

[75] Inventor: Dennis M. Zimmerman, Mooresville, Ind.

[73] Assignee: Eli Lilly and Company, Indianapolis, Ind.

[21] Appl. No.: 737,957

[22] Filed: Nov. 2, 1976

[51] Int. Cl.$^2$ .................. C07D 223/32; A61K 31/55
[52] U.S. Cl. .................... 260/239 BB; 260/465 D; 260/239.3 BB; 424/244; 560/37; 560/42
[58] Field of Search .................... 260/239 BB

[56] References Cited

U.S. PATENT DOCUMENTS

| 4,001,247 | 1/1977 | Zimmerman et al. | 260/289 D |
| 4,001,248 | 1/1977 | Zimmerman et al. | 260/289 D |

FOREIGN PATENT DOCUMENTS 802557  11/1973  Belgium .................. 260/289 D

OTHER PUBLICATIONS

Halford et al., J. Org. Chem., 17, pp. 1276–1280, (1952).
Braun et al., "Berichte," 56B, pp. 690–696, (1923).
Braun et al., "Berichte," 58B, pp. 2765–2767, (1925).

*Primary Examiner*—Donald G. Daus
*Assistant Examiner*—D. B. Springer
*Attorney, Agent, or Firm*—Charles W. Ashbrook; Everet F. Smith

[57] ABSTRACT

2-Substituted-5a-aryl-decahydrocyclopent[c]azepines are useful as analgesics having mixed narcotic antagonist and agonist properties.

20 Claims, No Drawings

DECAHYDROCYCLOPENT[c]AZEPINES

BACKGROUND OF THE INVENTION

Morphine is the natural alkaloid which gives opium its analgesic actions. It has been known and used for centuries and still today is the standard against which new analgesics are measured. Extensive chemical modifications of morphine have produced analgesic substances of widely differing potency and addictive properties. Codeine, for example, is the methyl ethyl of morphine, and is a mild analgesic with only slight physical dependance liability. In contrast, the diacetyl derivative of morphine, heroin, is a powerful agonist with extremely high physical dependance liability. In addition to morphine and codeine, and many semisynthetic derivatives of naturally occurring opium alkaloids, there exist several structurally distinct chemical classes of drugs which display pharmacological properties related to those of morphine. Clinically useful drugs are found among the morphinans, benzomorphans, methadones, phenylpiperidines, and propionanilides.

Recently several new drugs having varied analgesic agonist and antagonist properties with varying degrees of physical dependance liabilities have been synthesized, and in some cases can be viewed as morphine part-structures. For example, certain decahydroisoquinolines having a hydroxyphenyl group attached at the ring junction para to the isoquinoline nitrogen atom can be viewed as a morphine part-structure. Such compounds are the subject of Belgian Pat. No. 802,557.

An object of this invention is to provide certain 2-substituted-5a-aryl-decahydrocyclopent[c]azepines which can be viewed as being structurally related to certain morphine part-structures such as the aforementioned morphinans, benzomorphans, and isoquinoline derivatives. The compounds provided by this invention have not heretofore been described, as no method for their preparation has been available. Additionally, the compounds of this invention display an unpredictable variation in analgesic antagonist and agonist properties, with decreased physical dependance liability.

SUMMARY OF THE INVENTION

This invention concerns cyclopent[c]azepines. More particularly, this invention provides decahydrocyclopent[c]azepines having the general structural formula

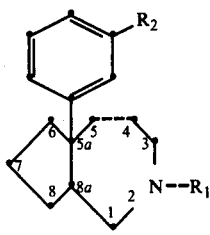

wherein: $R_1$ is hydrogen, $C_1$–$C_8$ alkyl, $CH_2R_3$ in which $R_3$ is $C_2$–$C_7$ alkenyl, $C_3$–$C_6$ cycloalkyl, furyl, or tetrahydrofuryl;

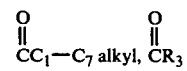

in which n is an integer from 0 to 3, m is 0 to 1, X is CO, CHOH, CH=CH, S or O, except that when n is 0, X is other than S or O, and when m is 0, n is other than 0, and $R_4$ and $R_5$ independently are hydrogen, $C_1$–$C_3$ alkyl, or halogen; and $R_2$ is hydrogen, hydroxy, $C_1$–$C_3$ alkoxy, or $C_1$–$C_3$ alkanoyloxy. Also included within the scope of this invention are the pharmaceutically acceptable acid addition salts of the compounds having the above formula. A preferred group of compounds comprehended by this invention are those of the above formula wherein $R_2$ is $C_1$–$C_3$ alkoxy or hydroxy, and particularly those wherein $R_2$ is hydroxy. Especially preferred compounds are those wherein $R_1$ is alkyl, alkenyl, or cycloalkylmethyl. Additionally included within the scope of this invention are the intermediate compounds having the above formula wherein $R_1$ is $$\overset{O}{\underset{\|}{C}}C_1-C_7 \text{ alkyl}, \overset{O}{\underset{\|}{C}}R_3$$

in which $R_3$ has the above defined meaning, and

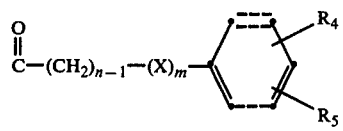

in which n, m, X, $R_4$ and $R_5$ have the above defined meaning.

DETAILED DESCRIPTION OF THE INVENTION

As hereinabove noted, this invention provides decahydrocyclopent[c]azepines having the above formula. Such compounds can be named as 5-azoazulenes or 7-azoazulenes; however, the preferred decahydrocyclopent[c]azepine nomenclature will be used throughout this specification.

Although a majority of the compounds provided by this invention are substituted at the nitrogen atom, (ie. compounds of the above formula wherein $R_1$ is other than H) which is the 2-position according to the above-described numbering system, the unsubstituted decahydrocyclopent[c]azepines, (compounds of the above formula wherein $R_1$ is hydrogen), are of particular importance as intermediates since they are readily converted to the 2-substituted decahydrocyclopent[c]azepines of this invention which are useful analgesics and analgesic antagonists, and intermediates therefor. Such pharmacologically useful 2-substituted decahydrocyclopent[c]azepines of this invention have the above formula when $R_1$ is $C_1$–$C_8$ alkyl such as methyl, ethyl, n-propyl, n-pentyl, isopropyl, n-butyl, 1-methylbutyl, 2-ethylpentyl, n-hexyl, 3-ethylhexyl, 1,1-dimethylhexyl, 1,2-dimethylpentyl, 1,2,3-trimethylbutyl, 1-ethylhexyl, n-octyl, isooctyl, and related groups. $R_1$ is also defined as $CH_2R_3$ wherein $R_3$ is $C_2$–$C_7$ alkenyl, $C_3$–$C_6$ cycloalkyl, furyl or tetrahydrofuryl. Examples of such $R_1$ groups include 2-propenyl or allyl, 3-butenyl, 2-methyl-2- pentenyl, 2,2-dimethyl-3-hexenyl, 3-ethyl-2-pentenyl, 3-methyl-4-heptenyl, 4-ethyl-2-hexenyl, 5-heptenyl, 2-methyl-4-heptenyl, cyclopropylmethyl, cyclobutylmethyl, cyclopentylmethyl, cyclohexylmethyl, 2-furylmethyl, 2-tetrahydrofurylmethyl, and 3-tetrahydrofurylmethyl. $R_1$ is also defined as a group of the formula

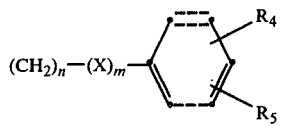

in which n is 0, 1, 2, or 3; m is 0 or 1; X is CO, CHOH, CH=CH, S or O, except that when n is 0, X is other than S or O; and when m is 0, n is other than 0; and $R_4$ and $R_5$ independently are hydrogen, $C_1$–$C_3$ alkyl, or halogen. The term halogen as used herein includes fluorine, bromine, chlorine and iodine. $C_1$–$C_3$ alkyl groups include methyl, ethyl, n-propyl and isopropyl. Representative examples of $R_1$ defined by the above formula include phenylmethyl, 2-phenylethyl, 2-(3,4-dichlorophenyl)ethyl, 3-(2-methyl-5-ethylphenyl)propyl, benzoylmethyl, 2-(4-fluorophenylcarbonyl)ethyl, phenoxymethyl, 2-(3-chloro-4-ethylphenoxy)ethyl, phenylthiomethyl, 2-(4,5-dimethylphenyl)-2-hydroxyethyl, 2-(2,6-diiodophenylthio)ethyl, 3-(3-bromophenylthio)propyl, and related groups.

As hereinabove noted, Belgian Pat. No. 802,557 discloses certain 4a-aryl-decahydroisoquinolines which are useful as analgesics and narcotic antagonists. Such compounds are prepared by cyclizing a 1-cyano-6-aryl-6-alkoxycarbonylmethyl-cyclohex-1-ene by reaction with an acid to provide a 1,3-dioxo-4a-aryl-octahydroisoquinoline, which then is reduced to the corresponding decahydroisoquinoline. The compounds of this invention are prepared utilizing similar reaction steps applied to novel intermediates. For example, a 1-alkoxycarbonyl-2-aryl-2-(2-cyanoethyl)cyclopentane is reduced to a 1-alkoxycarbonyl-2-alkyl-2-(3-aminopropyl)cyclopentane which is then cyclized to a 1-oxo-5a-aryl-decahydrocyclopent[c]azepine. Reduction of the 1-oxo group of the latter-named compound then provides a compound of this invention. The preparation of the compounds of this invention, however, requires as intermediates compounds not heretofore known, nor available by a known procedure. The discussion of the preparation of the compounds of this invention will additionally include a discussion of the preparation of intermediates which are thus required.

Generally, the decahydrocyclopent[c]azepines of this invention are prepared by reducing a 1-alkoxycarbonyl-2-aryl-2-(2-cyanoethyl)cyclopentane to the corresponding 1-alkoxycarbonyl-2-aryl-2-(3-aminopropyl)cyclopentane. The amino group of the 2-(3-aminopropyl) moiety of such cyclopentane derivative readily attacks the carbonyl group of the 1-alkoxycarbonyl moiety to expel a mole of a lower alkyl alcohol and thus form a cyclic amide, namely a 1-oxo-5a-aryl-decahydrocyclopent[c]azepine. Reduction of the 1-oxo group of such decahydrocyclopent[c]azepine derivative affords a compound of this invention. Such synthetic route is depicted below:

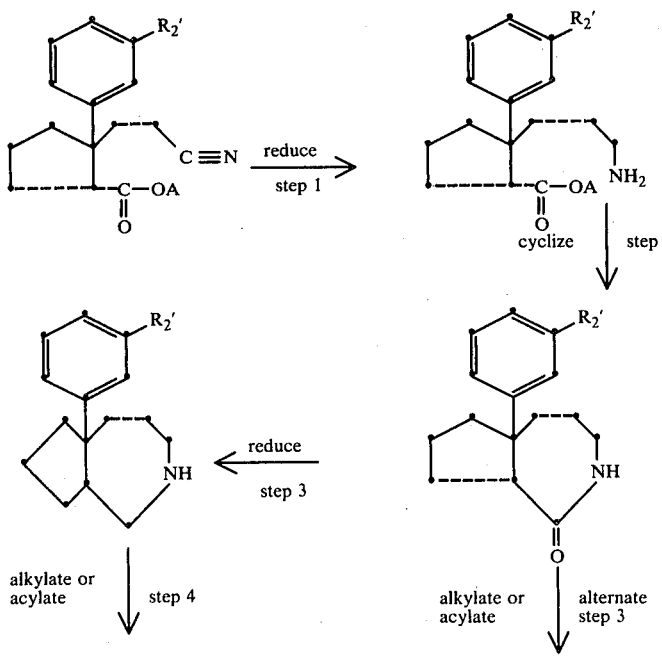

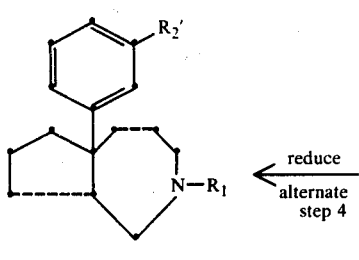 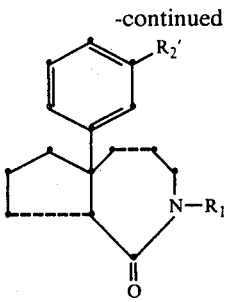

-continued wherein $R_2'$ is hydrogen or $C_1$–$C_3$ alkoxy, and A is lower alkyl such as methyl and ethyl.

Reduction of the cyano group of a 1-alkoxycarbonyl-2-aryl-2-(2-cyanoethyl)cyclopentane, step 1 in the above reaction scheme, can be accomplished by catalytic hydrogenation in the presence of a catalyst such as Raney nickel. Such hydrogenation reaction generally is carried out in an organic solvent such as methanol or ethanol, and under a hydrogen gas atmosphere at a pressure of from about 100 psi to about 1000 psi. The reaction is best carried out at a temperature of about 50° to 200° C., and usually is substantially complete within six to twenty-four hours. The product, a 1-alkoxycarbonyl-2-aryl-2-(3-aminopropyl)cyclopentane, is easily isolated by filtering the reaction mixture to remove the hydrogenation catalyst, and then evaporating the reaction solvent from the filtrate. The aminopropylcyclopentane derivative so formed can be further purified if desired; however, it is preferred to simply dissolve such cyclopentane derivative in a suitable solvent and heat the solution in order to condense the amino group with the alkoxycarbonyl group so as to effect cyclization to provide a bicyclic amide, specifically a 1-oxo-5a-aryl-decahydrocyclopent[c]azepine. The cyclization generally is carried out by simply dissolving the 1-alkoxycarbonyl-2-aryl-2-(3-aminopropyl)cyclopentane in a solvent such as a xylene, dioxane, dimethylformamide, or the like, and heating such solution to a temperature within the range of about 80° to about 200° C. for a period of time of from 24 to 120 hours. For example, an aminoethylcyclopentane derivative such as 1-ethoxycarbonyl-2-phenyl-2-(3-aminopropyl)cyclopentane can be dissolved in a solvent such as dioxane and heated to about 130° C. for about 72 hours to effect cyclization to afford 1-oxo-5a-phenyl-decahydrocyclopent[c]azepine. The decahydrocyclopent[c]azepine so formed is readily isolated by removing the reaction solvent, for instance by evaporation under reduced pressure, and further purification can be accomplished if desired by routine procedures such as crystallization or chromatography. Typical decahydrocyclopent[c]azepines thus formed include:

1-oxo-5a-(3-methoxyphenyl)-decahydrocyclopent[c]azepine;
1-oxo-5a-(3-ethoxyphenyl)-decahydrocyclopent[c]azepine;
1-oxo-5a-(3-isopropoxyphenyl)-decahydrocyclopent[c]azepine; and the like.

The 1-oxo-5a-aryl-decahydrocyclopent[c]azepines so formed can be alkylated or acylated (alternate step 3 in the above reaction scheme) at the 2-position to provide a 1-oxo-(2-alkyl- or 2-acyl)-5a-aryl-decahydrocyclopent[c]azepine, which compound can then be reduced at the 1-oxo group (alternate step 4) to provide a compound of this invention or an intermediate. Preferably, the 1-oxo-5a-aryl-decahydrocyclopent[c]azepine can first be reduced at the 1-oxo group (step 3) to provide a 5a-aryl-decahydrocyclopent[c]azepine, which can then be alkylated or acylated (step 4) at the 2-position to provide the corresponding 2-substituted-5a-aryl-decahydrocyclopent[c]azepine contemplated by this invention. For example, reaction of a 1-oxo-5a-aryl-decahydrocyclopent[c]azepine with a reducing agent such as lithium aluminum hydride or sodium bis (2-methoxyethoxy)aluminum hydride effects reduction of the 1-oxo group to provide the corresponding 5a-aryl-decahydrocyclopent[c]azepine. Such reduction reactions normally are accomplished by reacting about equimolar quantities of a 1-oxo-decahydrocyclopent[c]azepine and a reducing agent in a solvent such as benzene or diethyl ether at a temperature of about 20° to 80° C. The reduction of the 1-oxo group typically is substantially complete within ten to twenty hours, and the product, 2-unsubstituted-5a-aryl-decahydrocyclopent[c]azepine, is readily isolated by simply adding the reaction mixture to an aqueous base, such as aqueous potassium hydroxide or the like, and then extracting the product therefrom into a suitable water-immiscible solvent such as benzene, diethyl ether, dichloromethane, or related solvents. Evaporation of the solvent from the extract then leaves the 5a-aryl-decahydrocyclopent[c]azepine, which generally can be further purified if desired by distillation or chromatography. Such 5a-aryl-decahydrocyclopent[c]azepines are of particular importance as intermediates since they are easily alkylated or acylated at the 2-position thereby leading to other compounds of the invention and intermediates therefor. Typical 5a-aryl-decahydrocyclopent[c]azepines routinely prepared as described above include:

5a-phenyl-decahydrocyclopent[c]azepine;
5a-(3-methoxyphenyl)decahydrocyclopent[c]azepine;
5a-(3-ethoxyphenyl)decahydrocyclopent[c]azepine; and
5a-(3-propoxyphenyl)decahydrocyclopent[c]azepine.

In general, the aforementioned reduction of a 1-oxo-5a-aryl-decahydrocyclopent[c]azepine by reaction with a reducing agent such as lithium aluminum hydride or sodium bis(2-methoxyethoxy)aluminum hydride affords predominantly the corresponding 5a-aryl-decahydrocyclopent[c]azepine in which the 5a-aryl group is oriented on the side of the molecule opposite from the 8a-hydrogen atom. Such orientation of the 5a-aryl and 8a-hydrogen atoms is said to be trans. In contrast, when a 1-oxo-5a-aryl-decahydrocyclopent[c]azepine is first alkylated at the 2-position, for instance by reaction with methyl iodide and a base such as sodium amide, followed by reduction of the 1-oxo group, the corresponding 2-substituted-5a-aryl-decahydrocyclopent[c]azepine is predominantly the cis isomer, in which the 5a-aryl group and the 8a-hydrogen atom are oriented on the same side of the plane of the decahydrocyclopent[c]azepine ring system. It should be noted, however, that reaction of a trans-2-unsubstituted-5a-aryl-decahydrocyclopent[c]azepine with exactly one equivalent of a strong base such as lithium diisopropylamide and an alkylating agent such as methyl iodide effects only alkylation at the 2-position and not epimerization of the 8a-hydrogen atom, thus providing the corresponding trans-2-alkylated-5a-aryl-decahydrocyclopent[c]azepine.

Alkylation of either a 5a-aryl-decahydrocyclopent[c]azepine or a 1-oxo-5a-aryl-decahydrocyclopent[c]azepine is accomplished by reacting such compound with an alkylating agent such as an alkyl halide, alkyl tosylate, or alkyl azide, in the presence of a base such as potassium carbonate, sodium amide, or sodium bicarbonate, and in a solvent such as acetone or dimethylformamide. Typical alkylating agents include $C_1$–$C_8$ alkyl halides such as methyl iodide, ethyl bromide, 3-methylpentylbromide, 2-ethylhexyl chloride, and n-octyl iodide. Also included are alkenyl halides such as allyl bromide, 3-butenyl chloride, 5-hexenyl iodide, 2-methyl-4-hexenyl bromide, and 2,3-dimethyl-3-pentenylbromide; and cycloalkylmethyl halides such as cyclopropylmethyl chloride, cyclobutylmethyl iodide, cyclohexylmethyl bromide, as well as other related alkyl halides such as benzoylmethyl chloride, phenoxyethyl bromide, phenylthiopropyl iodide, 3-(3,4-dichlorobenzoyl)propyl iodide and the like. The 5a-aryl-decahydrocyclopent[c]azepine, or the 1-oxo-derivative, and alkylating agent are normally incorporated in approximately equimolar quantities, and the base which is utilized is generally incorporated in an equimolar quantity or in excess if desired. The reaction can be conducted at a temperature within the range of about 0° to about 180° C., and is substantially complete within about 2 to 10 hours. The product is then isolated by diluting the reaction mixture with water and then extracting the product therefrom into a water-immiscible solvent such as diethyl ether. Evaporation of the solvent from such extracts provides the product, namely a 2-substituted-5a-aryl-decahydrocyclopent[c]azepine, or the corresponding 1-oxo derivative, which can be further purified if desired by crystallization, distillation, chromatography, or similar purification techniques. Alternatively, the decahydrocyclopentazepine can be converted to an acid addition salt by reaction with an inorganic acid such as sulfuric acid, hydrobromic acid, or phosphoric acid, or an organic acid such as succinic or maleic acid. Such 2-substituted-5a-aryl-decahydrocyclopent[c]azepine acid addition salts characteristically are highly crystalline solids which are readily purified by recrystallization. If desired, such purified salt can be treated with a base such as sodium hydroxide to effect conversion to the decahydrocyclopent[c]azepine as the free base in a more purified state.

As hereinbefore noted, the 2-unsubstituted-5a-aryl-decahydrocyclopent[c]azepines prepared as above described can additionally be acylated at the 2-position to provide an N-acyl-decahydrocyclopentazepine, which compound can then be reduced at the N-acyl carbonyl moiety to provide a pharmaceutically active analgesic of this invention. The N-acylated compounds of the invention have the above formula wherein $R_1$ is

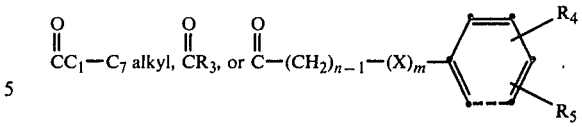

Reduction of the carbonyl group of such N-acyl derivatives clearly leads to compounds wherein $R_1$ is $C_1$–$C_8$ alkyl, $CH_2R_3$, or

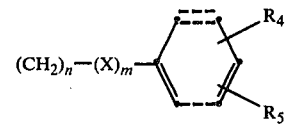

respectively. Commonly used acylating agents include acyl halides and anhydrides, including mixed anhydrides. The N-acylated compounds are prepared by normal acylation procedures known to those skilled in the art. For example, a compound such as 5a-phenyl-decahydrocyclopent[c]azepine can be reacted with about an equimolar quantity of an acylating agent such as 3,4-dimethylphenylacetyl chloride in an organic solvent such as dichloromethane, acetone, or tetrahydrofuran, to afford the corresponding 2-(3,4-dimethylphenylacetyl)-5a-phenyldecahydrocyclopent[c]azepine. Such acylation reactions are generally carried out in the presence of a base such as sodium bicarbonate to act as an acid-binding agent. The reaction usually is conducted at a temperature of about 0° to 100° C., and is generally complete within about 1 to 8 hours. The N-acylated-decahydrocyclopentazepine is readily isolated by simply removing the reaction solvent, for instance by evaporation. Acylating agents commonly utilized in such acylation reactions include acetyl chloride, 2-(tetrahydrofuryl)formyl chloride, 3-furylacetyl bromide, 3-hexenoyl chloride, cyclohexylformyl bromide, phenylacetyl iodide, 3-(2-fluorophenyl)propionyl bromide, phenylthiopropionyl bromide, 4-(3-methylphenoxy)butyryl bromide, acetic anhydride, benzoic formic anhydride, and the like. The 2-acylated-decahydrocyclopentazepine derivatives so formed are useful intermediates and are converted to an analgesic compound of this invention by reduction of the acyl group, for example by reaction with a reducing agent such as lithium aluminum hydride or catalytic hydrogenation. For example, reaction of a compound such as 2-(2-bromo-5-ethylphenyl)acetyl-5a-(3-methoxyphenyl)-decahydrocyclopent[c]azepine with about an equimolar quantity of lithium aluminum hydride in a solvent such as diethyl ether effects reduction of the 2-acyl carbonyl group to provide, for example, 2-(2-bromo-5-ethylphenyl)ethyl-5a-(3-methoxyphenyl)-decahydrocyclopent[c]azepine.

Further modifications can be made on the 2-substituted-5a-aryl-decahydrocyclopent[c]azepines which are prepared as hereinbefore described. For example, when the 2-substituent of such decahydrocyclopentazepine derivative bears a carbonyl group, for instance when the 2-substituent is a group such as benzoylmethyl, 2-(3,4-dibromobenzoyl)ethyl, or 3-(4-ethylbenzoyl)propyl, such carbonyl group can be reduced to the corresponding alcohol by reaction with a reducing agent such as lithium aluminum hydride. For example, reaction of 2-(benzoylmethyl)-5a-phenyl-decahydrocyclopent[c]azepine with about an equimolar quantity of lithium aluminum hydride in a solvent such as tetrahydrofuran effects reduction of the benzoyl carbonyl group to provide 2-(2-hydroxy-2-phenyl)ethyl-5a-phenyl-decahydrocyclopent[c]azepine. Such compounds can be dehydrated if desired to form the corresponding alkenyl derivatives, that is compounds of the above formula wherein X is CH=CH.

Compounds provided by this invention which have a hydroxyl group at the 3-position of the 5a-aryl substituent; that is, 5a-(3-hydroxyphenyl)-decahydrocyclopent[c]azepines, are derived from the corresponding 5a-(3-methoxyphenyl)-decahydrocyclopent[c]azepines by normal de-etherification reactions utilizing reagents such as hydrobromic acid in acetic acid, pyridine hydrochloride, boron tribromide, and the like. For example, reaction of a decahydrocyclopentazepine such as 2-(3-tetrahydrofurylmethyl)-5a-(3-methoxyphenyl)-decahydrocyclopent[c]azepine with pyridine hydrochloride at a temperature of about 50° to about 200° C. for 12 to 24 hours effects cleavage of the methoxy group of the 5a-methoxyphenyl moiety to provide a 5a-hydroxyphenyl moiety, thus providing, for example, 2-(3-tetrahydrofurylmethyl)-5a-(3-hydroxyphenyl)-decahydrocyclopent[c]azepine. Such product is isolated from the reaction mixture by diluting the solution with water and making the reaction mixture alkaline, for instance by adding sodium hydroxide or ammonium hydroxide, and then extracting the product from such aqueous alkaline solution into a solvent such as diethyl ether. Evaporation of the solvent from the extract then affords the desired compound, which generally needs no further purification.

The 2-substituted-5a-(3-hydroxyphenyl)-decahydrocyclopent[c]azepines so prepared are useful as analgesics, and also as intermediates in that acylation of such compounds at the hydroxyl group of the 5a-phenyl moiety provides the 2-substituted-5a-(3-alkanoyloxyphenyl)-decahydrocyclopent[c]azepines of the invention. Such acylation reactions are accomplished utilizing standard procedures. For example, reaction of a 2-substituted-5a-(3-hydroxyphenyl)-decahydrocyclopent[c]azepine with an acylating agent such as formyl chloride, acetyl bromide, or propionyl anhydride, in an organic solvent such as acetone or dichloromethane and in the presence of a base such as sodium bicarbonate or pyridine, effects acylation to provide the corresponding 2-substituted-5a-(3-alkanoyloxyphenyl)-decahydrocyclopent[c]azepine.

It may in certain instances be desirable to convert a 2-substituted-5a-aryl-decahydrocyclopent[c]azepine to the corresponding 2-unsubstituted derivative. Groups which can be readily attached at the 2-position and which can be as readily removed include the methyl and benzyl groups. For example, a 2-methyl-5a-aryl-decahydrocyclopent[c]azepine can be reacted with a haloformate such as phenyl chloroformate or ethyl chloroformate to afford the corresponding carbamate, which, when treated with an aqueous base such as aqueous sodium hydroxide or potassium hydroxide, is converted to the 2-unsubstituted-decahydrocyclopent[c]azepine derivative.

Similarly, 2-benzyl-5a-aryl-decahydrocyclopent[c]azepines are conveniently converted to the corresponding 2-unsubstituted derivative by catalytic hydrogenation. For example, reaction of 2-benzyl-5a-phenyl-decahydrocyclopent[c]azepine with hydrogen gas in the presence of a catalyst such as palladium suspended on carbon in a solvent such as ethyl alcohol effects debenzylation to provide, for example, 5a-phenyl-decahydrocyclopent[c]azepine.

Once the 2-unsubstituted-5a-aryl-decahydrocyclopent[c]azepine are prepared according to any of the above described procedures, alkylation or acylation at the 2-position then can be accomplished by routine procedures as set forth above to provide active compounds of the invention or intermediates leading to active compounds. For example, alkylation of 5a-(3-methoxyphenyl)-decahydrocyclopent[c]azepine by reaction with an alkylating agent such as 3-furylmethyl-chloride affords 2-(3-furylmethyl)-5a-(3-methoxyphenyl)-decahydrocyclopent[c]azepine. Alternatively, 5a-(3-methoxyphenyl)-decahydrocyclopent[c]azepine can be acylated by reaction with an acylating agent such as 3-furylformyl bromide to afford 2-(3-furylformyl)-5a-(3-methoxyphenyl)-decahydrocyclopent[c]azepine. The latter compound is useful as an intermediate since reduction of the 2-acyl moiety, for instance by catalytic hydrogenation or by reaction with lithium aluminum hydride, affords the corresponding analgesic, namely 2-(3-furylmethyl)-5a-(3-methoxyphenyl)-decahydrocyclopent[c]azepine.

As hereinabove pointed out, the 5a-aryl-decahydrocyclopent[c]azepines provided by this invention exist as stereoisomers since the 5a and 8a positions are asymmetric centers, thus providing dl-cis and dl-trans racemates. It is not necessarily required that the cis and trans racemates be separated, since both sets are useful analgesic agents. However, it may be desirable to obtain predominantly a dl-trans-decahydrocyclopent[c]azepine, or alternatively the dl-cis racemate, as one set of isomers may have a significantly different ratio of agonist and antagonist properties when compared to the corresponding set of isomers. As hereinbefore noted, the decahydrocyclopent[c]azepines of this invention are prepared by cyclization of a 1-alkoxycarbonyl-2-aryl-2-(3-aminopropyl)cyclopentane, followed by reduction. It is believed that such cyclization reaction provides predominantly the corresponding dl-5a,8a-trans decahydrocyclopent[c]azepine derivative. Reduction of such trans derivative with lithium aluminum hydride or the like affords the corresponding dl-trans-5a-aryl-decahydrocyclopent[c]azepine. Alkylation in the presence of a base such as sodium amide of such dl-trans derivative prior to reduction effects epimerization of the 8a-hydrogen atom along with alkylation at the 2-position to provide a dl-5a,8a-cis-2-substituted-5a-aryl-decahydrocyclopent[c]azepine.

When a mixture of cis and trans-decahydrocyclopent[c]azepines is formed and it is desired to separate such mixture into its components, such separation can be accomplished by any of a number of routine methods including chromatography and crystallization of salts. For example, a mixture of dl-cis and dl-trans-5a-aryl-decahydrocyclopent[c]azepines can be converted to the corresponding hydrochloride salt, and the dl-cis isomer can be fractionally crystallized from the mixture leaving primarily the dl-trans isomers. The dl-trans isomers can be purified by conversion to the corresponding picrate salt by reaction with picric acid and crystallization, followed by reaction with a base to obtain the dl-trans-5a-aryl-decahydrocyclopent[c]azepine free base. It is intended that reference to a decahydrocyclopent[c]azepine as used throughout this specification includes the mixtures of stereoisomers as well as the separated isomers and racemates which have useful pharmacological properties.

As has already been pointed out, the decahydrocyclopent[c]azepines of this invention are basic substances capable of forming non-toxic pharmaceutically acceptable acid addition salts by reaction with any of a number of inorganic and organic acids. Acids which are commonly used to form such salts include inorganic acids such as hydrochloric acid, hydrobromic acid, sulfuric acid, phosphoric acid, perchloric acid, nitric acid, and the like. Routinely used organic acids include acetic acid, propionic acid, maleic acid, succinic acid, palmitic acid, stearic acid, benzoic acid, adipic acid, picric acid, and para-toluenesulfonic acid. A typical method for preparing non-toxic pharmaceutically acceptable acid addition salts of this invention comprises dissolving the decahydrocyclopent[c]azepine free base in an organic solvent such as diethyl ether and then adding an acid, such as gaseous hydrogen bromide for instance, to the solution, thereby precipitating the acid addition salt as a solid. Such salts can be collected by filtration and recrystallized if desired from solvents such as diisopropyl ether and isopropyl alcohol.

The following list of 5a-aryl-decahydrocyclopent[c]azepines is representative of those prepared according to the above-described procedures and which are encompassed within this invention.

5a-phenyl-decahydrocyclopent[c]azepine;
5a-(3-methoxyphenyl)-decahydrocyclopent[c]azepine hydrobromide;
5a-(3-hydroxyphenyl)-decahydrocyclopent[c]azepine;
5a-(3-acetoxyphenyl)-decahydrocyclopent[c]azepine;
2-methyl-5a-phenyl-decahydrocyclopent[c]azepine;
2-ethyl-5a-(3-ethoxyphenyl)-decahydrocyclopent[c]azepine hydroiodide;
2-(3-methylhexyl)-5a-(3-propoxyphenyl)-decahydrocyclopent[c]azepine hydrogen acetate;
2-n-octyl-5a-(3-formyloxyphenyl)-decahydrocyclopent[c]azepine;
2-(3-butenyl)-5a-(3-hydroxyphenyl)-decahydrocyclopent[c]azepine;
2-(2-methyl-3-hexenyl)-5a-(3-methoxyphenyl)-decahydrocyclopent[c]azepine hydrophosphate;
2-(7-octenyl)-5a-(3-acetoxyphenyl)-decahydrocyclopent[c]azepine;
2-cyclopropylmethyl-5a-(3-ethoxyphenyl)-decahydrocyclopent[c]azepine;
2-cyclobutylformyl-5a-(3-hydroxyphenyl)-decahydrocyclopent[c]azepine;
2-cyclohexylmethyl-5a-(3-propionoxyphenyl)-decahydrocyclopent[c]azepine;
2-(3-tetrahydrofurylmethyl)-5a-(3-methoxyphenyl)-decahydrocyclopent[c]azepine;
2-benzyl-5a-phenyl-decahydrocyclopent[c]-azepine hydroiodide;
2-(3-chlorophenyl)methyl-5a-(3-acetoxyphenyl)-decahydrocyclopent[c]azepine;
2-[3-(2,5-dimethylphenyl)propionyl]-5a-(3-hydroxyphenyl)-decahydrocyclopent[c]azepine;
2-(4-isopropylbenzoylmethyl)-5a-phenyl-decahydrocyclopent[c]azepine;
2-(2,3-dibromophenylthiomethyl)-5a-(3-ethoxyphenyl)-decahydrocyclopent[c]azepine tartrate;
2-[2-(2-bromo-4-ethylphenyl)ethyl]-5a-(3-methoxyphenyl)-decahydrocyclopent[c]azepine hydrochloride;
2-[3-(3-ethyl-5-n-propylphenyl)propyl]-5a-phenyl-decahydrocyclopent[c]azepine;
2-phenoxymethyl-5a-phenyldecahydrocyclopent[c]azepine hydrosulfate;
2-[3-(3,5-dichlorophenyl)-3-hydroxy]propyl-5a-(3-acetoxyphenyl)-decahydrocyclopent[c]azepine hydroiodide;
2-[2-(3,4-diethylbenzoyl)ethyl]-5a-(3-methoxyphenyl)-decahydrocyclopent[c]azepine;
2-phenylhydroxymethyl-5a-phenyl-decahydrocyclopent[c]azepine para-toluenesulfonate;
2-(3,5-di-n-propylbenzoyl)methyl-5a-(3-hydroxyphenyl)-decahydrocyclopent[c]azepine;
2-phenylthiomethyl-5a-(3-hydroxyphenyl)-decahydrocyclopent[c]azepine;
2-phenoxyacetyl-5a-(3-ethoxyphenyl)-decahydrocyclopent[c]azepine; and
2-(3,4-diethylphenylthiomethyl)-5a-(3-methoxyphenyl)-decahydrocyclopent[c]azepine hydrochloride.

As hereinbefore noted, the decahydrocyclopentazepines provided by this invention require for their preparation certain intermediate compounds heretofore unknown and unavailable by routine procedures. For example, the aforementioned 1-alkoxycarbonyl-2-aryl-2-(2-cyanoethyl)cyclopentane which is reduced and then cyclized as previously described is derived from a cyclohexanone derivative, specifically a 2-aryl-2-(2-cyanoethyl)-6-diazocyclohexanone. Such diazocyclohexanone derivative is prepared from a 2-aryl-2-(2-cyanoethyl)-6-formylcyclohexanone, which in turn is derived from a 2-aryl-2-(2-cyanoethyl)-cyclohexanone, which itself is prepared from a commercially available 2-arylcyclohexanone such as 2-phenylcyclohexanone, 2-(3-methoxyphenyl)cyclohexanone, 2-(3-ethoxyphenyl)cyclohexanone, and the like. Such 2-arylcyclohexanones are cyanoethylated by reaction with acrylonitrile in the presence of a base such as sodium hydride or potassium tert.-butoxide. For example, 2-(3-methoxyphenyl)cyclohexanone can be reacted with about an equimolar quantity of acrylonitrile and sodium hydride in a solvent such as benzene to effect alkylation at the 2-position and thus provide 2-(3-methoxyphenyl)-2-(2-cyanoethyl)cyclohexanone. Such 2-aryl-2-(2-cyanoethyl)cyclohexanones next are formylated at the 6-position to provide the corresponding 2-aryl-2-(2-cyanoethyl)-6-formylcyclohexanones. The formylation reaction is carried out by reacting the 6-unsubstituted cyclohexanone derivative with about an equimolar quantity of a strong base such metallic sodium and in the presence of an equimolar quantity or an excess of a lower alkyl formate such as methyl formate or ethyl formate. The reaction is best carried out in a solvent such as benzene or diethyl ether, and normally is complete within 24 to 72 hours. As an example, a 2-aryl-2-(2-cyanoethyl)cyclohexanone such as 2-(3-ethoxyphenyl)-2-(2-cyanoethyl)cyclohexanone is reacted with metallic sodium and methyl formate in diethyl ether to provide 2-(3-ethoxyphenyl)-2-(2-cyanoethyl)-6-formylcyclohexanone.

Reaction of a formyl cyclohexanone derivative with para-toluenesulfonylazide effects displacement of the formyl group by a diazo moiety to provide a diazocyclohexanone derivative. For example, a formyl cyclohexanone derivative such as 2-phenyl-2-(2-cyanoethyl)-6-formylcyclohexanone can be reacted with about an equimolar quantity of para-toluene-sulfonylazide in the presence of dimethylamine or diethylamine, in an organic solvent such as diethyl ether, to provide, for instance, 2-phenyl-2-(2-cyanoethyl)-6-diazocyclohexanone.

Such diazocyclohexanone derivative next is photolyzed in the presence of a lower alkyl alcohol such as methanol or ethanol to effect expulsion of nitrogen gas with concomittant ring contraction and lower alkyl ester formation. Such photolysis is accomplished by simply stirring a solution of the diazocyclohexanone derivative in an alcoholic solvent such as ethanol under a light source of about 3000 angstroms. For example, a diazocyclohexanone such as 2-(3-propoxyphenyl)-2-(2-cyanoethyl)-6-diazocyclohexanone can be dissolved in a solvent such as n-propanol and stirred at about 25° C. under a quartz lamp at about 3000 angstroms to provide, for example, 1-(propoxycarbonyl)-2-(3-propoxyphenyl)-2-(2-cyanoethyl)cyclopentane. Such 1-alkoxycarbonyl-2-aryl-2-(2-cyanoethyl)cyclopentanes are then reduced and cyclized as hereinbefore described to provide the 5a-aryl-decahydrocyclopent[c]azepines of this invention.

As hereinbefore pointed out, the 5a-aryl-decahydrocyclopentazepines of this invention are useful in the treatment of pain, and can then be used to effect analgesia in a subject suffering from pain and in need of treatment. The compounds of this invention have mixed analgesic agonist and analgesic antagonist properties, and are thus capable of producing analgesia in a mammal while not displaying a large incidence of addiction liability. Such ability of the compounds disclosed herein to cause analgesic agonist as well as analgesic antagonist effects in mammals is thus responsible for the decrease in any addictive properties of a particular drug caused by its opiate-like analgesic action. The compounds are particularly useful in combating the undesirable side effects of drugs such as morphine.

The biological properties possessed by the compounds of this invention have been evaluated by testing the compounds in standard animal assays routinely used to measure analgesic action attributable to a certain compound. Such assays include the mouse-writhing test and the rat tail jerk assay. For example, dl-trans-2-(2-phenylethyl)-5a-(3-methoxyphenyl)-decahydrocyclopent[c]azepine hydrobromide demonstrated a 61 percent inhibition of writhing after thirty minutes when administered orally at the rate of 100 mg/kg. of body weight to a mouse suffering from acetic acid induced writhing. The corresponding cis racemate demonstrated 69 percent inhibition in writhing in a similar assay. Similarly tested were the dl-cis- and dl-trans-racemates of 2-methyl-5a-(3-hydroxyphenyl)-decahydrocyclopent[c]azepine hydrochloride, both of which produced a 100 percent inhibition in writhing in mice at an oral dose of 100 mg/kg. Such rate of inhibition was measured thirty minutes and again 90 minutes after administration of the drug to the test animal.

The 5a-aryl-decahydrocyclopent[c]azepines provided by this invention can be formulated for convenient oral or parenteral administration to a mammal in need of treatment. It may be desirable to utilize a non-toxic pharmaceutically acceptable acid addition salt of the decahydrocyclopentazepines when the dosage is to be by the oral route, since such salts are highly soluble in aqueous media and thus are easily formulated for convenient oral administration. One or more pharmacologically active compounds of this invention are formulated for use by being admixed with any of a number of commonly used diluents, excipients, carriers, and the like. Such diluents and carriers include starch, sucrose, lactose, calcium sulfate, sodium benzoate, magnesium stearate, and the like. The compounds of this invention can additionally be combined with one or more known analgesic agents, such as propoxyphene, acetaminophen, aspirin, and the like. The formulations typically will contain a sufficient quantity of a compound of this invention so that the daily dosage of such compound will be within about 0.1 to about 50.0 mg. per kg. of animal body weight. Such formulations can be molded into tablets or encapsulated within gelatin capsules, or suspensions or solutions can be prepared by mixing a compound of the invention with propylene glycol, vegetable oils, saline solution, or the like. A typical formulation will include, for example, about 100 mg. of a decahydrocyclopentazepine such as 2-cyclobutylmethyl-5a-(3-hydroxyphenyl)-decahydrocyclopent[c]azepine hydrogen phosphate, admixed with about 200 mg. of starch, 20 mg. of ethyl benzoate, and 10 mg. of propoxyphene hydrochloride. Such mixture is molded into a tablet, which then is administered orally to a subject at the rate of about 1 to 3 tablets per day or as needed.

The following detailed examples are provided by way of illustration of particular aspects of the invention. The examples are purely illustrative and are not intended to be limiting in any way.

EXAMPLE 1

2-(3-methoxyphenyl)-2-(2-cyanoethyl)-6-formylcyclohexanone

A solution of 270 g. of 2-(3-methoxyphenyl)-2-(2-cyanoethyl)-cyclohexanone in 2180 ml. of diethyl ether containing 113 g. of ethyl formate and 31.86 g. of metallic sodium was stirred at 25° C. for sixty-six hours. The reaction mixture was then poured into 1000 ml. of ice-water, and the ethereal layer was separated therefrom. The aqueous layer was acidified to pH 6.5 by the addition of 1N hydrochloric acid, and the acidic aqueous layer was extracted with fresh diethyl ether. The ethereal extracts were washed with water and dried. Removal of the solvent by evaporation under reduced pressure provided 284 g. of 2-(3-methoxyphenyl)-2-(2-cyanoethyl)-6-formylcyclohexanone.

Following the procedure set forth in Example 1 there was prepared 2-phenyl-2-(2-cyanoethyl)-6-formylcyclohexanone from 2-phenyl-2-(2-cyanoethyl)cyclohexanone and ethylformate.

EXAMPLE 2

2-(3-methoxyphenyl)-2-(2-cyanoethyl)-6-diazocyclohexanone

A solution of 206.2 g. of 2-(3-methoxyphenyl)-2-(2-cyanoethyl)-6-formylcyclohexanone in 1000 ml. of diethyl ether was stirred at 25° C. while a solution of 183.2 g. of diethylamine in 300 ml. of diethyl ether was added dropwise over thirty minutes. The reaction mixture was then stirred for two hours at 25° C. and then cooled to 5° C. in an ice-water bath and stirred while a solution of 206.2 g. of p-toluenesulfonylazide in 200 ml. of diethyl ether was added dropwise over thirty minutes. Following complete addition of the ethereal solution of p-toluenesulfonylazide to the reaction mixture, the mixture was allowed to warm to 25° C. and was stirred for ten hours. The reaction mixture then was washed with water and dried, and the solvent was removed therefrom by evaporation under reduced pressure at about 20° C., thus providing an oil. The oil was triturated with diethyl ether, and the portion which failed to dissolved in the diethyl ether was removed by filtration. The precipitate was washed several times with fresh diethyl ether, and the ethereal extracts were combined and concentrated to dryness by evaporation under reduced pressure at 20° C. to afford 215 g. of 2-(3-methoxyphenyl)-2-(2-cyanoethyl)-6-diazocyclohexanone.

Similarly prepared was 2-phenyl-2-(2-cyanoethyl)-6-diazocyclohexanone from 2-phenyl-2-(2-cyanoethyl)-6-formylcyclohexanone.

EXAMPLE 3

1-Methoxycarbonyl-2-(3-methoxyphenyl)-2-(2-cyanoethyl)cyclopentane

A solution of 179 g. of 2-(3-methoxyphenyl)-2-(2-cyanoethyl)-6-diazocyclohexanone in 100 ml. of anhydrous methanol was stirred at 25° C. while nitrogen gas was bubbled through the reaction mixture and the reaction mixture was photolyzed with a quartz lamp at 3000 angstroms for seventy-two hours. The solvent was then removed from the reaction mixture by evaporation under reduced pressure to provide the product as an oil. The oil was distilled to yield 120 g. of 1-methoxycarbonyl-2-(3-methoxyphenyl)-2-(2-cyanoethyl)cyclopentane. B.P. 184°–188° C. at 0.5 torr.

Analysis calc. for $C_{16}H_{21}NO_3$: Theory: C, 69.79; H, 7.69; N, 5.09. Found: C, 69.43; H, 7.35; N, 5.46.

Following the procedure of Example 3, 2-phenyl-2-(2-cyanoethyl)-6-diazocyclohexanone was photolyzed to provide 1-methoxycarbonyl-2-phenyl-2-(2-cyanoethyl)cyclopentane.

EXAMPLE 4

1-Oxo-5a-(3-methoxyphenyl)-decahydrocyclopent[c]azepine

A solution of 57.4 g. of 1-methoxycarbonyl-2-(3-methoxyphenyl)-2-(2-cyanoethyl)cyclopentane in 280 ml. of ethyl alcohol containing 19.4 g. of Raney nickel and 78 ml. of liquid ammonia was stirred at 150° C. under a hydrogen gas atmosphere at 700 psi for ten hours. The reaction mixture then was filtered, and the filtrate was concentrated to dryness by evaporation of the solvent under reduced pressure. The residual oil so formed was dissolved in 270 ml. of xylene and heated at reflux for three days. Removal of the solvent by evaporation under reduced pressure provided the product as a solid residue. The solid so formed was recrystallized from 150 ml. of diisopropyl ether and 400 ml. of isopropyl alcohol to afford 25.0 g. of predominantly dl-trans-1-oxo-5a-(3-methoxyphenyl)-decahydrocyclopent[c]azepine. M.P. 191°–193° C.

Analysis cacl. for $C_{16}H_{21}NO_2$: Theory: C, 74.10; H, 8.16; N, 5.40. Found: C, 73.89; H, 7.94; N, 5.13.

1-Methoxycarbonyl-2-phenyl-2-(2-cyanoethyl)cyclopentane was reduced and cyclized according to the procedure of Example 4 to provide predominantly dl-trans-1-oxo-5a-phenyl-decahydrocyclopent[c]azepine.

EXAMPLE 5 dl-cis-1-Oxo-2-methyl-5a-(3-methoxyphenyl)-decahydrocyclopent[c]azepine

A solution of 5.0 g. of dl-trans-1-oxo-5a-(3-methoxyphenyl)-decahydrocyclopent[c]azepine in 40 ml. of anhydrous toluene was added dropwise over thirty minutes to a stirred solution of 1.2 g. of sodium amide in 40 ml. of anhydrous toluene. The reaction mixture was heated at reflux for four hours, and then cooled to 25° C. and stirred while a solution of 4 g. of methyl iodide in 40 ml. of toluene was added in one portion. The reaction mixture was next heated to reflux and stirred for thirteen hours. After cooling the reaction mixture again to 25° C., 100 ml. of water was added dropwise over fifteen minutes. The aqueous layer was then separated, and the organic layer was washed with water, dried, and the solvent was removed by evaporation under reduced pressure to provide 5.3 g. of predominantly dl-cis-1-oxo-2-methyl-5a-(3-methoxyphenyl)-decahydrocyclopent[a]azepine. The product so formed was recrystallized three times from diisopropyl alcohol to afford pure dl-cis-1-oxo-2-methyl-5a-(3-methoxyphenyl)-decahydrocyclopent[c]azepine. M.P. 103°–104° C.

Analysis calc. for $C_{17}H_{23}NO_2$: Theory: C, 74.69; H, 8.48; N, 5.12. Found: C, 74.56; H, 8.25; N, 5.09.

EXAMPLE 6 dl-trans-1-Oxo-2-methyl-5a-(3-methoxyphenyl)-decahydrocyclopent[c]azepine

A solution of 5.0 g. of dl-trans-1-oxo-5-(3-methoxyphenyl)-decahydrocyclopent[c]azepine in 15 ml. of hexamethylphosphortriamide containing 10 ml. of tetrahydrofuran was added in one portion to a solution of lithium diisopropylamide prepared by reacting 12.18 ml. of n-butyl lithium with 1.95 g. of diisopropylamine in 25 ml. of tetrahydrofuran. The reaction mixture was stirred at about 10° C. for thirty minutes. The reaction mixture was then cooled to 0° C. and stirred while 3.29 g. of methyl iodide was added dropwise over thirty minutes. The reaction mixture was stirred for ninety minutes at 5° to 10° C., and then warmed to 25° C. and stirred for twelve hours. The reaction mixture next was added to 300 ml. of saturated aqueous sodium chloride solution, and the product was extracted therefrom into diethyl ether. The ethereal extracts were washed with water, dried, and the solvent was removed by evaporation under reduced pressure to provide 5.25 g. of the product as an oil which slowly crystallized. Recrystallization of the product so formed from diisopropyl ether and isopropyl alcohol afforded predominantly dl-trans-1-oxo-2-methyl-5a-(3-methoxyphenyl)-decahydrocyclopent[c]azepine. M.P. 96°–99° C.

Analysis calc. for $C_{17}H_{23}NO_2$: Theory: C, 74.69; H, 8.48; N, 5.12. Found: C, 74.45; H, 8.38; N, 5.04.

EXAMPLE 7

5a-(3-methoxyphenyl)-decahydrocyclopent[c]azepine

To a solution of 95 ml. of a seventy percent benzene solution of sodium bis(2-methoxyethoxy)aluminum hydride, (Red-al ®), was added dropwise over one hour a solution of 27 g. of dl-trans-1-oxo-5a-(3-methoxyphenyl)-decahydrocyclopent[c]azepine in 400 ml. of benzene. The reaction mixture then was heated at reflux and stirred for fifteen hours. After cooling the reaction mixture to 25° C., the solution was poured into 1000 ml. of 1N sodium hydroxide solution. The aqueous alkaline mixture was extracted several times with diethyl ether, and the ethereal extracts were combined, washed with water, and dried. Removal of the solvent by evaporation under reduced pressure afforded 21.5 g. of dl-trans-5a-(3-methoxyphenyl)-decahydrocyclopent[c]azepine. B.P. 154°–157° C. at 0.1 torr.

Analysis calc. for $C_{16}H_{23}NO$: Theory: C, 78.32; H, 9.45; N, 5.71. Found: C, 78.21; H, 9.27; N, 5.49.

Following the procedure set out in Example 7, dl-trans-1-oxo-2-methyl-5a-(3-methoxyphenyl)-decahydrocyclopent[c]azepine was reacted with Red-al ® in benzene to provide dl-trans-2-methyl-5a-(3-methoxyphenyl)-decahydrocyclopent[c]azepine. B.P. 130°–140° C. at 0.05 torr.

EXAMPLE 8 dl-trans-5a-(3-methoxyphenyl)-decahydrocyclopent[c]azepine

A solution of 11.4 g. of dl-trans-1-oxo-5a-(3-methoxyphenyl)-decahydrocyclopent[c]azepine in 75 ml. of tetrahydrofuran was added dropwise over thirty minutes to a stirred solution of 2.2 g. of lithium aluminum hydride in 150 ml. of tetrahydrofuran. The reaction mixture was heated at reflux and stirred for five hours, and then cooled to 25° C. The reaction mixture was then added to 30 ml. of ethyl acetate, and the solution was diluted with 50 ml. of saturated aqueous ammonium tartrate solution. The tetrahydrofuran layer containing the product was decanted, diluted with diethyl ether, washed with water and dried. Removal of the solvent by evaporation under reduced pressure provided 8.9 g. of dl-trans-5a-(3-methoxyphenyl)-decahydrocyclopent[c]azepine as an oil. The oil so formed was distilled to provide 3.7 g. of dl-trans-5a-(3-methoxyphenyl)-decahydrocyclopent[c]azepine. B.P. 154°–157° C. at 0.1 torr.

Analysis calc. for $C_{16}H_{23}NO$: Theory: C, 78.32; H, 9.45; N, 5.71. Found: C, 78.18; H, 9.12; N, 5.37.

EXAMPLE 9

5a-(3-methoxyphenyl)-decahydrocyclopent[c]azepine

To a stirred solution of 14.4 g. of 2-methyl-5a-(3-methoxyphenyl)-decahydrocyclopent[c]azepine in 200 ml. of dichloromethane was added dropwise over thirty minutes to a stirred solution of 11.2 g. of phenyl chloroformate. The reaction mixture was then heated to reflux and stirred for four hours. The reaction mixture was then cooled to 25° C., and the solvent was removed therefrom by evaporation under reduced pressure to provide 2-phenoxycarbonyl-5a-(3-methoxyphenyl)-decahydrocyclopent[c]azepine as a solid. The solid thus formed was dissolved in 600 ml. of ethyl alcohol containing 140 ml. of 50 percent aqueous sodium hydroxide solution. The reaction mixture was heated at reflux and stirred for sixty hours. After cooling to 25° C., the reaction mixture was added to 500 ml. of water, and the aqueous solution was acidified to pH 2 by the addition of 12 N hydrochloric acid. The aqueous acidic solution was washed with diethyl ether to remove any unreacted carbamate, and the aqueous acidic solution was then made alkaline by the addition of 50 percent aqueous sodium hydroxide solution. The aqueous alkaline solution was extracted with fresh diethyl ether. The ethereal extracts were combined, washed with water, and dried. Removal of the solvent by evaporation under reduced pressure provided 7 g. of 5a-(3-methoxyphenyl)-decahydrocyclopent[c]azepine. B.P. 136°–140° C. at 0.05 torr.

Analysis calc. for $C_{16}H_{21}NO$: Theory: C, 78.32; H, 9.45; N, 5.71. Found: C, 78.39; H, 9.26; N, 5.76.

EXAMPLE 10

2-(2-propenyl)-5a-(3-methoxyphenyl)-decahydrocyclopent[c]azepine hydrochloride

A solution of 1.8 g. of 5a-(3-methoxyphenyl)-decahydrocyclopent[c]azepine and 0.84 g. of allyl bromide in 20 ml. of N,N-dimethylformamide containing 0.84 g. of sodium bicarbonate was heated to reflux and stirred for four hours. The reaction mixture then was cooled to 25° C., poured into 200 ml. of water, and the product was extracted therefrom into diethyl ether. The ethereal extracts were combined, washed with water, and dried. Gaseous hydrogen chloride was added to the ethereal solution, and the product precipitated out of solution and was collected by filtration. The solid precipitate so formed was recrystallized from 30 ml. of diisopropyl ether and 50 ml. of isopropyl alcohol, affording 1.2 g. of 2-(2-propenyl)-5a-(3-methoxyphenyl)-decahydrocyclopent[c]azepine hydrochloride. M.P. 144°–146° C.

Analysis calc. for $C_{19}H_{28}NOCl$: Theory: C, 70.90; H, 8.77; N, 4.35. Found: C, 70.77; H, 8.67; N, 4.30.

EXAMPLE 11

2-Cyclopropylmethyl-5a-(3-methoxyphenyl)-decahydrocyclopent[c]azepine hydrochloride A solution of 1.1 g. of 5a-(3-methoxyphenyl)-decahydrocyclopent[c]azepine and 1.3 g. of cyclopropylformyl chloride in 20 ml. of N,N-dimethylformamide containing 1.4 g. of triethylamine was stirred at 25° C. for eight hours. The reaction mixture then was added to 200 ml. of water, and the aqueous solution was extracted several times with diethyl ether. The ethereal extracts were combined, and the solvent was removed therefrom by evaporation under reduced pressure to provide 2-cyclopropylformyl-5a-(3-methoxyphenyl)-decahydrocyclopent[c]azepine. The product so formed was dissolved in 70 ml. of tetrahydrofuran containing 1 g. of lithium aluminum hydride, and the reaction mixture was heated at reflux and stirred for three hours. The reaction mixture was then cooled to 25° C. and diluted by the dropwise addition of 30 ml. of ethyl acetate. The tetrahydrofuran solution was decanted, diluted with diethyl ether, washed with water, and dried. Removal of the solvent by evaporation under reduced pressure provided 2-cyclopropylmethyl-5a-(3-methoxyphenyl)-decahydrocyclopent[c]azepine as an oil. The oil so formed was dissolved in 50 ml. of diethyl ether through which was bubbled hydrogen chloride gas, thus forming the hydrochloride salt of the above-named compound, which precipitated out of solution. The precipitate was collected by filtration and recrystallized from 25 ml. of diisopropyl ether and 100 ml. of ethyl acetate to afford 0.75 g. of ethyl acetate to afford 0.75 g. of 2-cyclopropylmethyl-5a-(3-methoxyphenyl)-decahydrocyclopent[c]azepine hydrochloride. M.P. 154°–156° C.

Analysis calc. for $C_{20}H_{30}NOCl$: Theory: C, 71.51; H, 9.00; N, 4.17. Found: C, 71.21; H, 8.83; N, 4.36.

Following the procedure set forth in Example 11, dl-cis-5a-(3-methoxyphenyl)-decahydrocyclopent[c]azepine was acylated with phenylacetyl chloride to provide dl-cis-2-phenylacetyl-5a-(3-methoxyphenyl)-decahydrocyclopent[c]azepine. Reduction of the latter compound by reaction with lithium aluminum hydride afforded dl-cis-2-(2-phenylethyl)-5a-(3-methoxyphenyl)-decahydrocyclopent[c]azepine, which was converted to the corresponding hydrochloride salt. M.P. 95°–97.5° C.

Analysis calc. for $C_{24}H_{32}NOCl$: Theory: C, 74.68; H, 8.36; N, 3.63. Found: C, 74.42; H, 8.32; N. 3.61.

EXAMPLE 12 dl-cis-2-Methyl-5a-(3-hydroxyphenyl)-decahydrocyclopent[c]azepine hydrochloride

A solution of 3.4 g. of dl-cis-2-methyl-5a-(3-methoxyphenyl)-decahydrocyclopent[c]azepine in 23 ml. of glacial acetic acid containing 23 ml. of forty-eight percent aqueous hydrobromic acid was heated to reflux and stirred for fifteen hours. The reaction mixture then was cooled to 25° C. and added to 25 ml. of water. The aqueous mixture was made alkaline to pH 9.2 by the addition of ammonium hydroxide. The aqueous alkaline solution was extracted several times with diethyl ether, and the ethereal extracts were combined, washed with water, and dried. Removal of the solvent by evaporation under reduced pressure provided 2.6 g. of dl-cis-2-methyl-5a-(3-hydroxyphenyl)-decahydrocyclopent[c]azepine. The product so formed was dissolved in 200 ml. of fresh diethyl ether, and gaseous hydrogen chloride was bubbled through the solution, thus forming the hydrochloride salt which precipitated out of solution. The precipitate was collected by filtration and recrystallized from 150 ml. of diisopropyl ether and 275 ml. of isopropyl alcohol to provide 1.1 g. of dl-cis-2-methyl-5a-(3-hydroxyphenyl)-decahydrocyclopent[c]azepine hydrochloride. M.P. 179.5°–182° C.

Analysis calc. for $C_{16}H_{24}NOCl$: Theory: C, 68.19; H, 8.58; N, 4.97. Found: C, 67.91; H, 8.83; N, 4.99.

By following the procedure set forth in Example 12, dl-trans-2-methyl-5a-(3-methoxyphenyl)-decahydrocyclopent[c]azepine was converted to dl-trans-2-methyl-5a-(3-hydroxyphenyl)-decahydrocyclopent[c]azepine hydrochloride. M.P. 160°–162° C.

Analysis calc. for $C_{16}H_{24}NOCl$: Theory: C, 68.19; H, 8.58; N, 4.97. Found: C, 68.25; H, 8.38; N, 5.08.

EXAMPLE 13 dl-trans-2-(2-Phenylethyl)-5a-(3-methoxyphenyl)-decahydrocyclopent[c]azepine hydrobromide A solution of 3.5 g. of dl-trans-5a-(3-methoxyphenyl)-decahydrocyclopent[c]azepine in 52 ml. of methyl alcohol containing 3.2 g. of potassium carbonate and 17 ml. of water was stirred and cooled to 5°–10° C. in an ice bath while 3.2 g. of phenylacetyl chloride was added dropwise over thirty minutes. The reaction mixture was then warmed to 25° C. and stirred for an additional one hour. The solvent was next evaporated from the reaction mixture, leaving an oil which was dissolved in diethyl ether. The ethereal solution was washed with 5 percent aqueous sodium hydroxide, with 5 percent aqueous hydrochloric acid, and then with water, and dried. Removal of the solvent by evaporation under reduced pressure afforded dl-trans-2-phenylacetyl-5a-(3-methoxyphenyl)-decahydrocyclopent[c]azepine.

The product so formed was dissolved in 25 ml. of tetrahydrofuran and added dropwise over thirty minutes to a stirred solution of 3 g. of lithium aluminum hydride in 150 ml. of tetrahydrofuran at 25° C. The reaction mixture then was heated at reflux and stirred for four hours. The reaction mixture was cooled and diluted by the dropwise addition of 35 ml. of ethyl acetate and saturated aqueous ammonium tartrate to precipitate unreacted salts. The tetrahydrofuran layer was decanted, washed with water and dried. Removal of the solvent by evaporation under reduced pressure provided 2.51 g. of dl-trans-2-(2-phenylethyl)-5a-(3-methoxyphenyl)-decahydrocyclopent[c]azepine. The product so formed was dissolved in 150 ml. of diethyl ether and hydrogen bromide gas was bubbled through the solution thus precipitating the corresponding hydrobromide salt. The precipitate was collected by filtration and recrystallized from diisopropyl ether and isopropyl alcohol to afford 0.4 g. of dl-trans-2-(2-phenylethyl)-5a-(3-methoxyphenyl)-decahydrocyclopent[c]azepine hydrobromide. M.P. 170° C. dec.

Analysis calc. for $C_{24}H_{32}NOBr$: Theory: C, 66.97; H, 7.49; N, 3.25. Found: C, 67.13; H, 7.68; N, 3.03.

2-(2-phenylethyl)-5a-(3-methoxyphenyl)-decahydrocyclopent[c]azepine was similarly reacted with acetic acid in diethyl ether to provide 2-(2-phenylethyl)-5a-(3-methoxyphenyl)-decahydrocyclopent[c]azepine hydroacetate.

EXAMPLE 14

2-Isopentyl-5a-(3-propionoxyphenyl)-decahydrocyclopent[c]azepine

A solution of 2-isopentyl-5a-(3-hydroxyphenyl)-decahydrocyclopent[c]azepine in acetone containing sodium bicarbonate and water was stirred while a solution of propionyl chloride in acetone was added dropwise. The reaction mixture was stirred for several hours, and the organic solvent was then removed by evaporation under reduced pressure. The aqueous layer was then extracted several times with diethyl ether. The ethereal extracts were combined, washed with water, and dried. Evaporation of the solvent then provided 2-isopentyl-5a-(3-propionoxyphenyl)-decahydrocyclopent[c]azepine.

I claim:

1. A compound of the formula:

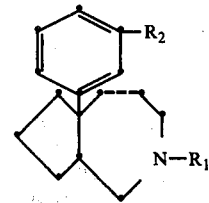

wherein:

$R_1$ is $C_1$–$C_8$ alkyl, $CH_2R_3$, benzyl, or 2-phenethyl, in which:

$R_3$ is $C_2$–$C_7$ alkenyl or $C_3$–$C_6$ cycloalkyl;

$R_2$ is hydrogen, hydroxy, or $C_1$–$C_3$ alkoxy; and the pharmaceutically acceptable acid addition salts thereof.

2. A compound of the formula:

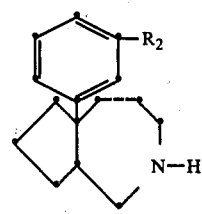

wherein: $R_2$ is hydrogen, hydroxy or $C_1$–$C_3$ alkoxy.

3. The compound of claim 2, said compound being 5a-phenyl-decahydrocyclopent[c]azepine.

4. The compound of claim 2, said compound being 5a-(3-hydroxyphenyl)-decahydrocyclopent[c]azepine.

5. A compound of claim 2 wherein $R_2$ is $C_1$–$C_3$ alkoxy.

6. The compound of claim 5, said compound being 5a-(3-methoxyphenyl)-decahydrocyclopent[c]azepine.

7. A compound of claim 1 wherein $R_1$ is $C_1$–$C_8$ alkyl.

8. A compound of claim 7 wherein $R_1$ is methyl.

9. The compound of claim 8, said compound being 2-methyl-5a-(3-methoxyphenyl)-decahydrocyclopent[c]azepine.

10. A compound of claim 1 wherein $R_1$ is $CH_2R_3$.

11. A compound of claim 10 wherein $R_3$ is $C_2$–$C_7$ alkenyl.

12. A compound of claim 10 wherein $R_3$ is $C_3$–$C_6$ cycloalkyl.

13. A compound of claim 12 wherein $R_3$ is cyclopropyl.

14. A compound of claim 1 wherein $R_1$ is benzyl or 2-phenethyl.

15. The compound of claim 14, said compound being 2-benzyl-5a-(3-methoxyphenyl)-decahydrocyclopent[c]azepine.

16. A compound of claim 1 as the pharmaceutically acceptable acid addition salt.

17. A compound of the formula

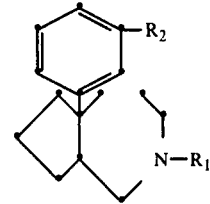

wherein:
$R_1$ is

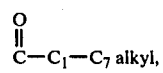

benzoyl, phenylacetyl, or

in which:
$R_3$ is $C_2$–$C_7$ alkenyl or $C_3$–$C_6$ cycloalkyl; and
$R_2$ is hydrogen, hydroxy or $C_1$–$C_3$ alkoxy.

18. A compound of claim 17 wherein $R_1$ is acetyl.

19. A compound of claim 17 wherein $R_1$ is cyclopropylformyl.

20. A compound of claim 17 wherein $R_1$ is benzoyl.

* * * * *